United States Patent
Sasaki et al.

(10) Patent No.: US 10,514,254 B2
(45) Date of Patent: Dec. 24, 2019

(54) ROAD SURFACE PROPERTY ACQUIRING METHOD AND ROAD SURFACE PROPERTY ACQUIRING DEVICE

(71) Applicant: TOPCON CORPORATION, Tokyo (JP)

(72) Inventors: You Sasaki, Tokyo (JP); Tadayuki Ito, Tokyo (JP)

(73) Assignee: TOPCON CORPORATION, Itabashi-ku, Tokyo (JP)

( * ) Notice: Subject to any disclaimer, the term of this patent is extended or adjusted under 35 U.S.C. 154(b) by 107 days.

(21) Appl. No.: 15/423,785

(22) Filed: Feb. 3, 2017

(65) Prior Publication Data
US 2017/0307368 A1    Oct. 26, 2017

(30) Foreign Application Priority Data
Feb. 4, 2016  (JP) .................................. 2016-020249

(51) Int. Cl.
| | |
|---|---|
| *G01B 11/30* | (2006.01) |
| *G06K 9/52* | (2006.01) |
| *G06K 9/00* | (2006.01) |
| *G01N 21/88* | (2006.01) |
| *G06K 9/46* | (2006.01) |

(52) U.S. Cl.
CPC ....... *G01B 11/303* (2013.01); *G01N 21/8851* (2013.01); *G06K 9/00791* (2013.01); *G06K 9/00798* (2013.01); *G06K 9/4642* (2013.01); *G06K 9/52* (2013.01)

(58) Field of Classification Search
CPC .................................................... G01B 11/303
USPC ........................................................ 356/600
See application file for complete search history.

(56) References Cited

U.S. PATENT DOCUMENTS

| 5,130,709 A * | 7/1992 | Toyama ................. G01C 21/28 340/990 |
| 6,233,510 B1 * | 5/2001 | Platner ................... B60G 13/16 382/104 |
| 2003/0069668 A1 | 4/2003 | Zurn |
| 2009/0295917 A1 * | 12/2009 | Zhang ................ G06K 9/00798 348/119 |

(Continued)

FOREIGN PATENT DOCUMENTS

| JP | H10-288516 A | 10/1998 |
| JP | 2010175756 A | 8/2010 |

(Continued)

*Primary Examiner* — Tarifur R Chowdhury
*Assistant Examiner* — Omar H Nixon
(74) *Attorney, Agent, or Firm* — Chiesa Shahinian & Giantomasi PC

(57) ABSTRACT

To rapidly and reliably measure a road surface property using measurement results and determination results of a road surface in the past. A vehicle mounted with a road surface property acquiring device is guided to a specified point on a road and measurement is carried out. The past road surface data on a past road surface property is acquired, a present position of the vehicle is acquired, and a past road surface property image representing a feature amount of the road surface property in a range including the present position created based on the past road surface data is displayed; and the vehicle is guided from the present position to a specified area while measuring a state of the road surface with the road surface property acquiring device.

18 Claims, 12 Drawing Sheets

(56) References Cited

U.S. PATENT DOCUMENTS

| | | | |
|---|---|---|---|
| 2009/0310143 A1* | 12/2009 | Gardiner | E01C 23/01 356/600 |
| 2010/0088024 A1 | 4/2010 | Takahara et al. | |
| 2010/0182613 A1* | 7/2010 | Holton | G01P 3/366 356/600 |
| 2013/0103259 A1* | 4/2013 | Eng | B60G 17/019 701/37 |
| 2013/0266186 A1* | 10/2013 | Zhang | G06K 9/00798 382/104 |
| 2014/0081573 A1* | 3/2014 | Urmson | G01W 1/02 702/3 |
| 2014/0104424 A1* | 4/2014 | Zhang | B60R 1/00 348/148 |
| 2014/0184800 A1* | 7/2014 | Hirai | G01N 21/958 348/148 |
| 2014/0355839 A1* | 12/2014 | Bridgers | G06T 7/0004 382/108 |
| 2015/0169966 A1* | 6/2015 | Ishimaru | G08G 1/167 348/148 |
| 2015/0371095 A1* | 12/2015 | Hartmann | G06K 9/00791 348/148 |
| 2016/0171278 A1 | 6/2016 | Ponder et al. | |

FOREIGN PATENT DOCUMENTS

| | | |
|---|---|---|
| JP | 2013205130 A | 10/2013 |
| JP | 2014163707 A | 9/2014 |
| JP | 2015-031018 A | 2/2015 |

* cited by examiner

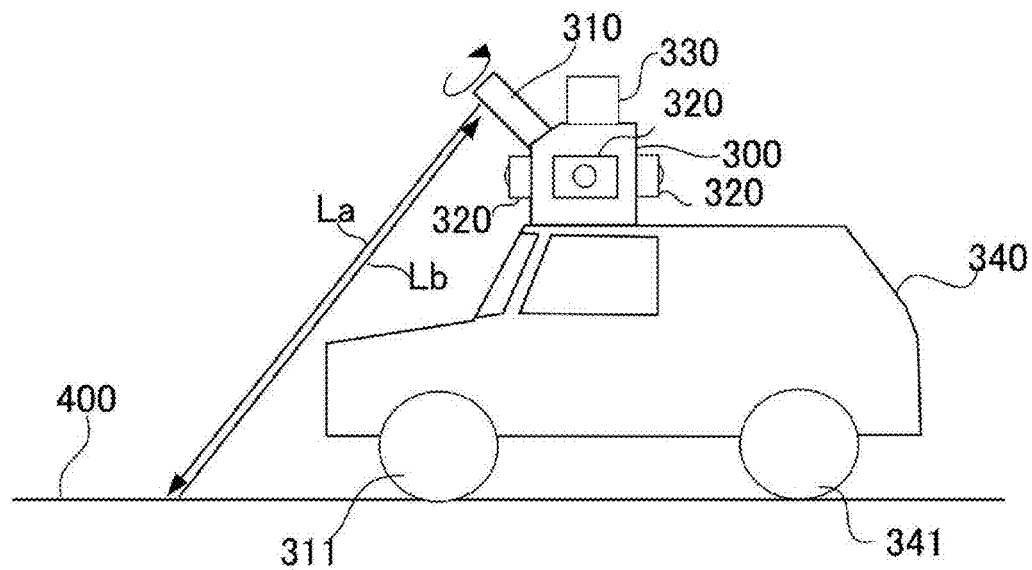
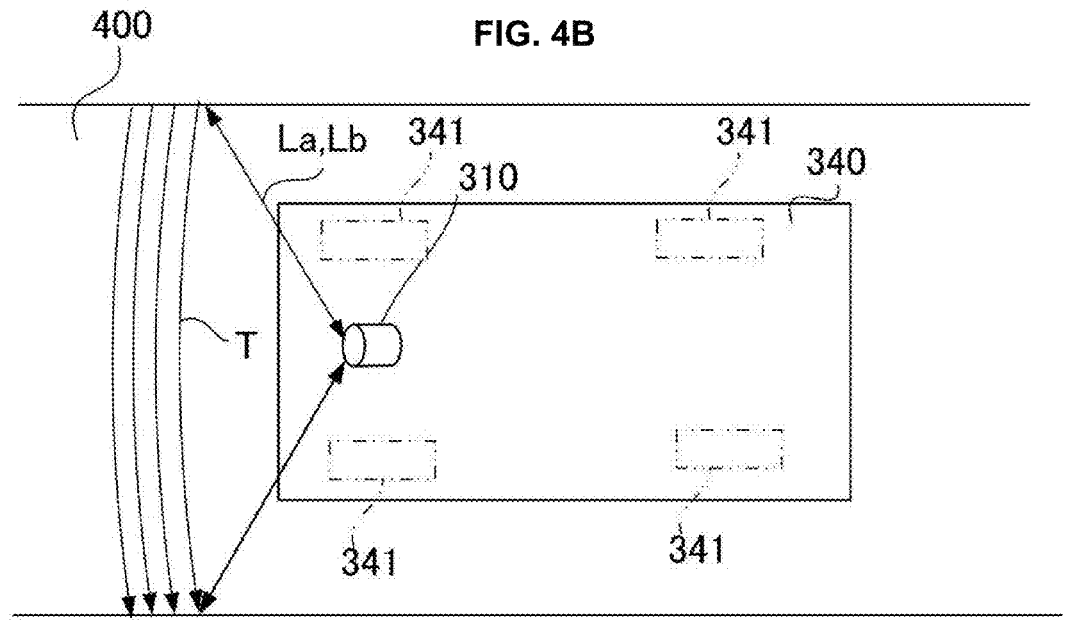

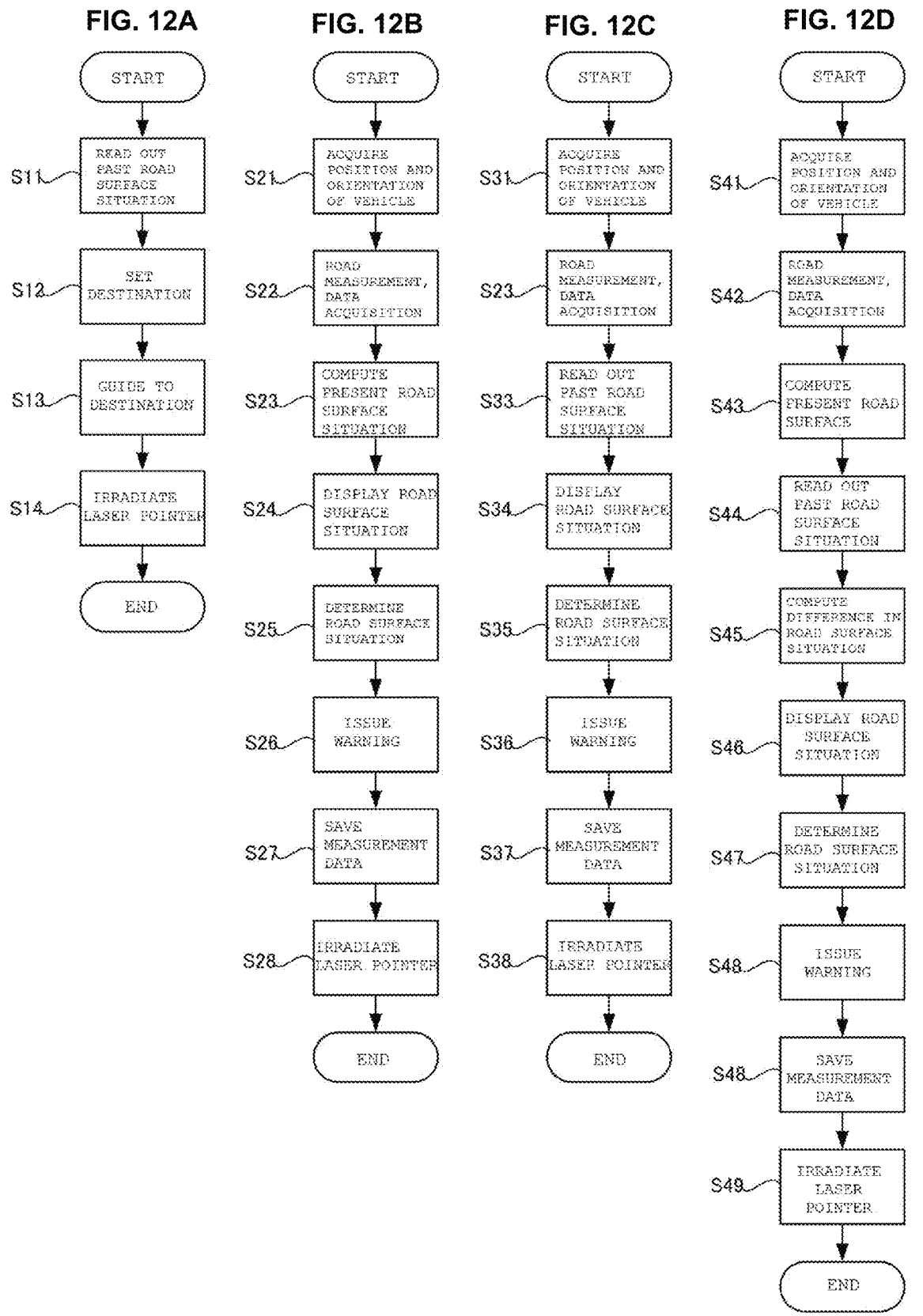

ROAD SURFACE PROPERTY ACQUIRING METHOD AND ROAD SURFACE PROPERTY ACQUIRING DEVICE

CROSS-REFERENCE TO RELATED APPLICATIONS

This application claims priority to Japanese Patent Application No. 2016-020249 filed on Feb. 4, 2016, which is incorporated herein by reference in its entirety.

TECHNICAL FIELD

The present invention relates to a road surface property acquiring method, and a road surface property acquiring device.

BACKGROUND OF THE INVENTION

Generally, roads produce splits and unevenness over time due to the passing of vehicles, and the like, and such splits and unevenness need to be repaired. In order to repair such roads, the road is inspected, and data on road surface property of the road, that is, data on a state of unevenness of the road surface are acquired. The data on the road surface property are acquired by measurement carried out by measuring personnel, or by causing a road surface property vehicle to travel along a predetermined path of a road to be measured. A device for irradiating a road surface with a scan light, and measuring a height of each point of the road surface is mounted on the road surface property vehicle.

Patent document 1 (i.e., Japanese Unexamined Patent Publication No. 10-288516) describes a device that projects light toward a plane while moving a moving body in a longitudinal direction of the plane, and measures a step difference of the plane according to the light projection result, the device having a configuration of including a means for detecting a moving distance, a light projecting means, a means for imaging a light irradiation line, a transverse direction data computing means for acquiring height data, a vertical direction data computing means, and a three-dimensional data computing means. According to such configuration, a technique in which the light is projected toward a plane RD from a moving body so that one irradiation line forms on the plane RD along a transverse direction W of the plane RD every time the moving body moves a predetermined distance, and an unevenness profile is acquired in real time by the various types of means is described.

Japanese Unexamined Patent Publication No. 10-288516 (i.e., Patent document 1)

In measuring the road surface property, it is efficient to carry out the measurement with reference to the measurement results of the road surface property and the road surface determination results in the past. For example, when carrying out maintenance to an area where splits, recesses, and projections formed in the past, and where the road surface state is poor, or when re-measuring such areas, it is not efficient to merely move aiming a point on a map and carry out the measurement. A technique that can rapidly and reliably measure the road surface property using the results of the measurement and the determination in the past is thus desired.

In light of the foregoing, it is an object of the present invention to provide a road surface property acquiring method and a road surface property acquiring device capable of rapidly and reliably measuring a road surface property using measurement results and determination results of a road surface in the past.

SUMMARY OF THE INVENTION

An invention described in claim 1 for solving the problem described above relates to a road surface property acquiring method of guiding a vehicle mounted with a road surface property acquiring device to a specified point on a road and carrying out measurement; the method including the steps of acquiring past road surface data on a past road surface property; acquiring a present position of the vehicle; displaying a past road surface property image representing a feature amount of the road surface property in a range including the present position created based on the past road surface data; and guiding the vehicle from the present position to a specified area while measuring a state of the road surface with the road surface property acquiring device.

According to the invention of claim 2, the road surface property acquiring method further includes a step of displaying a map image displaying a road.

According to the invention of claim 3, the road surface property acquiring method further includes the steps of acquiring present measurement data on a property of a road surface on which the vehicle is currently travelling; and displaying a present road surface property image representing a feature amount of the road surface property created based on the present measurement data with the past road surface property image.

According to the invention of claim 4, the road surface property acquiring method further includes a step of issuing a warning when the feature amount generated based on the past road surface property image at the present position exceeds a predefined value.

According to the invention of claim 5, the road surface property acquiring method further includes a step of saving measurement data in a region including the present position when the feature amount generated based on the past road surface property image at the present position exceeds a predefined value.

According to the invention of claim 6, the road surface property acquiring method further includes the steps of generating a difference value of the past road surface data and present measurement data on a property of a road surface on which the vehicle is currently travelling at the present position, and issuing a warning when the difference value exceeds a predefined value.

According to the invention of claim 7, the road surface property acquiring method further includes the steps of generating a difference value of the past road surface data and the present measurement data at the present position, and saving measurement data in a region including the present position when the difference value exceeds a predefined value.

According to the invention of claim 8, the road surface property acquiring method further includes the steps of setting a unit area, to become a unit of processing, based on the past road surface data; dividing the unit area into a plurality of sections and calculating a statistic from the past road surface data in each section; extracting a section having a statistic satisfying a predefined reference value; and detecting a deformed area candidate based on a changing amount of the statistic of the extracted section and a statistic of a section adjacent to the extracted section.

According to the invention of claim 9, the road surface property acquiring method further includes the steps of setting a region of a road exceeding the predefined value or a region of a road assumed as the deformed area candidate as a defective area; and irradiating and pointing the defective area with a laser pointer when close to the defective area.

An invention of claim 10 relates to a road surface property acquiring device of guiding a vehicle mounted with a road surface property acquiring device to a specified point on a road and carrying out measurement; the road surface property acquiring device including a means for acquiring past road surface data on a past road surface property; a means for acquiring a present position of the vehicle; a means for displaying a past road surface property image representing a feature amount of the road surface property in a range including the present position created based on the past road surface data; and a means for guiding the vehicle from the present position to a specified area while measuring a state of the road surface with the road surface property acquiring device.

According to the invention of claim 11, the road surface property acquiring device further includes a means for displaying a map image displaying a road.

According to the invention of claim 12, the road surface property acquiring device further includes a means for acquiring present measurement data on a property of a road surface on which the vehicle is currently travelling; and a means for displaying a present road surface property image representing a feature amount of the road surface property created based on the present measurement data with the past road surface property image.

According to the invention of claim 13, the road surface property acquiring device further includes a means for issuing a warning when the feature amount generated based on the past road surface property image at the present position exceeds a predefined value.

According to the invention of claim 14, the road surface property acquiring device further includes a means for saving measurement data in a region including the present position when the feature amount generated based on the past road surface property image at the present position exceeds a predefined value.

According to the invention of claim 15, the road surface property acquiring device further includes a means for generating a difference value of the past road surface data and present measurement data on a property of a road surface on which the vehicle is currently travelling at the present position, and a means for issuing a warning when the difference value exceeds a predefined value.

According to the invention of claim 16, the road surface property acquiring device further includes a means for generating a difference value of the past road surface data and the present measurement data at the present position, and a means for saving measurement data in a region including the present position when the difference value exceeds a predefined value.

According to the invention of claim 17, the road surface property acquiring device further includes a means for setting a unit area, to become a unit of processing, based on the past road surface data; a means for dividing the unit area into a plurality of sections and calculating a statistic from the past road surface data in each section; a means for extracting a section having a statistic satisfying a predefined reference value; and a means for detecting a deformed area candidate based on a changing amount of the statistic of the extracted section and a statistic of a section adjacent to the extracted section.

According to the invention of claim 18, the road surface property acquiring device further includes a means for setting a region of a road exceeding the predefined value or a region of a road assumed as the deformed area candidate as a defective area, and irradiating and pointing the defective area with a laser pointer when close to the defective area.

According to the present invention, the road surface property can be rapidly and reliably measured using the measurement results and the determination results of the road surface in the past.

In other words, according to the inventions described in claim 1 and claim 10, past road surface data on a past road surface property is acquired, a present position of the vehicle is acquired; a past road surface property image representing a feature amount of the road surface property in a range including the present position created based on the past road surface data is displayed; and the vehicle is guided from the present position to a specified area while measuring a state of the road surface with the road surface property acquiring device, so that the past road property can be displayed and the vehicle can be guided to a specified area while measuring the property of the road surface.

According to the inventions described in claim 2 and claim 11, the map image displaying the road is displayed so that vehicle can be easily guided to the specified area.

According to the inventions described in claim 3 and claim 12, present measurement data on a property of a road surface on which the vehicle is currently travelling is acquired; and a present road surface property image representing a feature amount of the road surface property created based on the present measurement data is displayed with the past road surface property image, so that the measurement of the road surface property can be carried out while comparing the present road surface property and the past road surface property.

According to the inventions described in claim 4 and claim 13, a warning is issued when the feature amount generated based on the past road surface property image at the present position exceeds a predefined value, and thus an area where the road surface property was poor in the past, and the like can be easily recognized.

According to the inventions described in claim 5 and claim 14, measurement data in a region including the present position is saved when the feature amount generated based on the past road surface property image at the present position exceeds a predefined value, and thus the measurement data can be stored for an area where the road surface property was poor in the past, and the like.

According to the inventions described in claim 6 and claim 15, a difference value of the past road surface data and present measurement data on a property of a road surface on which the vehicle is currently travelling is generated at the present position, and a warning is issued when the difference value exceeds a predefined value, and thus an area where the road surface property is poor compared to the past road surface property, and the like can be easily recognized.

According to the inventions described in claim 7 and claim 16, a difference value of the past road surface data and the present measurement data is generated at the present position, and measurement data in a region including the present position is saved when the difference value exceeds a predefined value, and thus the measurement data can be stored for an area where the road surface property is poor compared to the past.

According to the inventions described in claim 8 and claim 17, a unit area, to become a unit of processing, is set based on the past road surface data; the unit area is divided into a plurality of sections and a statistic is calculated from the past road surface data in each section; a section having a statistic satisfying a predefined reference value is extracted, and a deformed area candidate is detected based on a changing amount of the statistic of the extracted section and a statistic of a section adjacent to the extracted section, and thus a pot hole and the like serving as a recess, a protrusion between splits serving as a projection, and the like can be detected.

According to the inventions described in claim 9 and claim 18, a region of a road exceeding the predefined value or a region of a road assumed as the deformed area candidate is set as a defective area; and the defective area is irradiated and pointed out with a laser pointer when close to the defective area, and thus the defective area of the road surface can be easily grasped.

BRIEF DESCRIPTION OF DRAWINGS

FIG. 2A is a block diagram showing a configuration of a point group data generating means, FIG. 2B is a block diagram showing a configuration of a road surface evaluating means, and FIG. 2C is a block diagram showing a configuration of a deformed area detecting means;

FIG. 3B is a flowchart showing a processing procedure of the point group data generating means, FIG. 3B is a flowchart showing a processing procedure of the road surface evaluating means, and FIG. 3C is a flowchart showing a processing procedure of a deformed area candidate mark generating means;

FIGS. 4A and 4B are a schematic view showing a measurement state of a road surface by a data acquiring device, where FIG. 4A is a side view schematic showing a measurement state of a road surface by a data acquiring device and FIG. 4B is a plan view schematic thereof;

FIG. 5A is a perspective view of the measurement data, and FIG. 5B is a schematic view showing the measurement data and a measurement reference plane;

FIG. 6A is a schematic view showing the unit area, and FIG. 6B is a schematic view showing the point group data and a model plane MP;

FIG. 7A is a perspective schematic view showing the model plane MP and the point group data. FIG. 7B is a schematic view showing a spaced amount image, and FIG. 7C is a schematic view showing a road image;

FIG. 11A is a schematic view showing a section in a unit area, and FIG. 11B is a view showing a mark display on a road surface by a laser pointer; and FIGS. 12A, 12B, 12C, and 12D are a flowchart showing processes of the road surface property acquiring device.

DETAILED DESCRIPTION OF THE EXEMPLARY EMBODIMENTS

A road surface property acquiring method and a road surface property acquiring device according to a mode for carrying out the present invention will be described.

A road surface property acquiring method and a road surface property acquiring device according to the present embodiment display a spaced amount image, in which measurement data obtained in the previous measurement are shading coded or hue coded in correspondence with a spaced amount of point group data representing a separation amount from a model plane, and a past map image, in which an evaluation result of the road surface property is displayed, as a road surface property image during the data measurement to enable efficient acquisition of the road surface property data, and guides a vehicle, on which a data acquiring device is mounted, to an area where the road surface was rough the previous time, and the like. The determination result of the road surface property obtained by statistically processing the point group data can be displayed on the map. Furthermore, when approaching a location of rough road surface, notification can be made with display, sound, and the like during the measurement. The data on only the vicinity of the rough area can be stored.

The previous data can also be displayed to check temporal transition. Furthermore, a spaced amount from the model plane is calculated during the measurement, and display of the spaced amount image and a present road property image displaying the determination result of the road surface property, and warning display, audio warning, and the like of when the spaced amount exceeds a set threshold value are carried out. A difference value with the previous measurement data is also displayed. Moreover, a warning is issued when the difference value exceeds a defined value. A defective area of the road surface such as a pot hole where the spaced amount exceeds the defined value is pointed out with the laser pointer.

Accordingly, the present invention can carry out an efficient maintenance service of the road. Furthermore, the present invention can assist safety travelling as the road surface property can be grasped in real time during the measurement. Moreover, amount of saved data can be suppressed from becoming large as only the data on the necessary area is stored.

Figure 1:
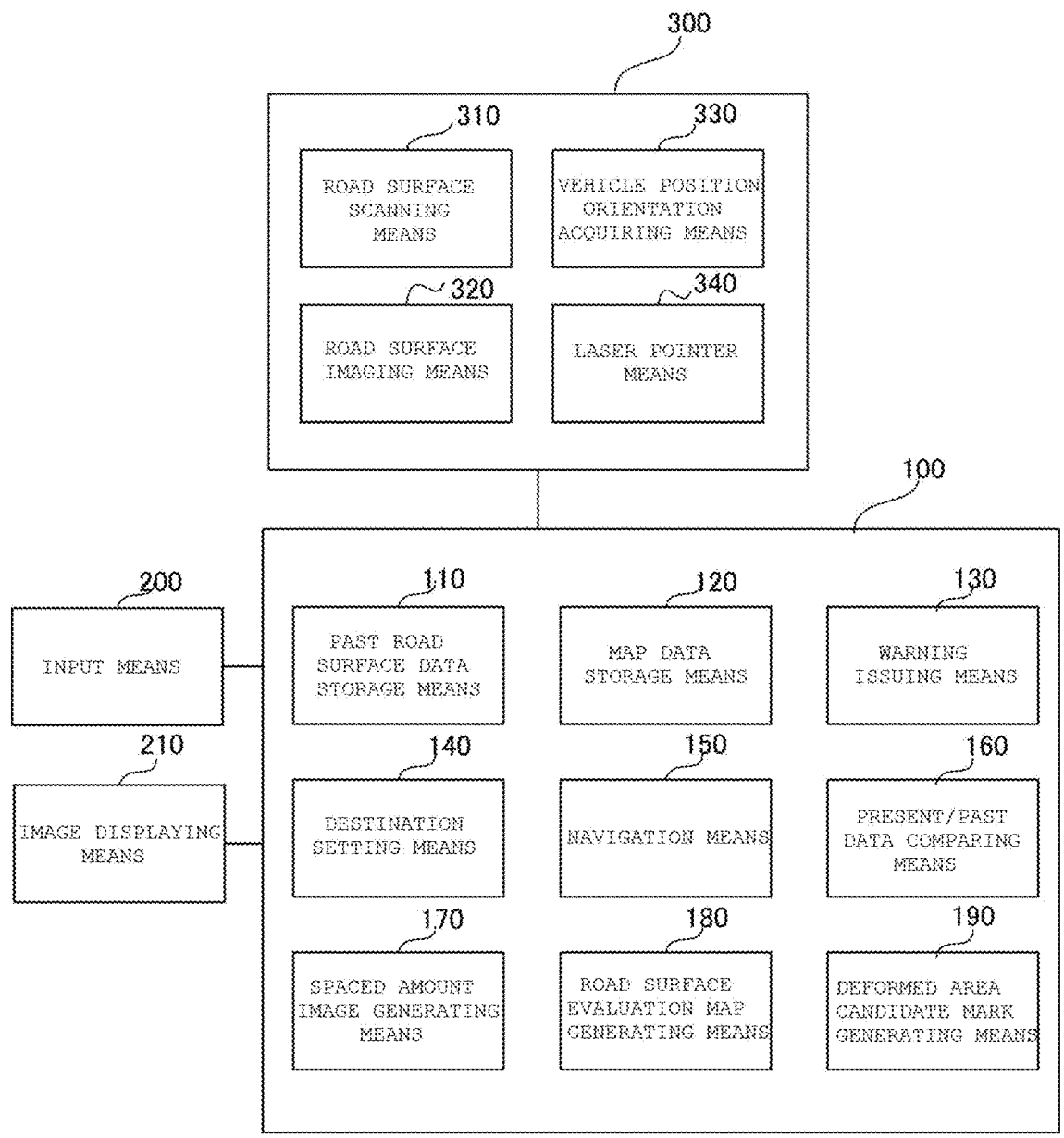
FIG. 1 is a block diagram showing a configuration of a road surface property acquiring device according to an embodiment of the present invention.
Figure 2A:
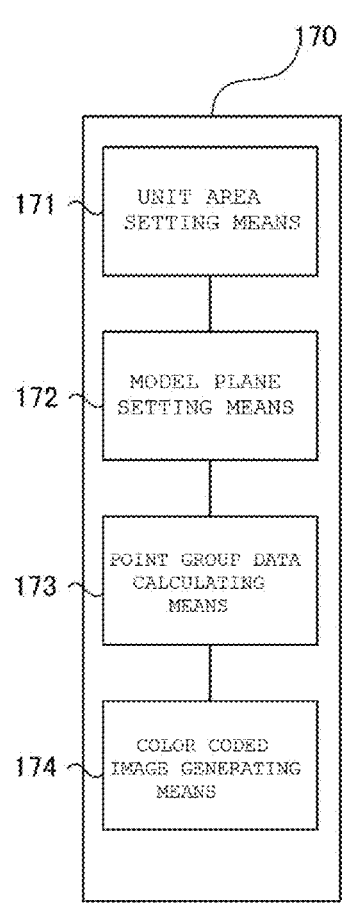
FIGS. 2A, 2B, and 2C show a configuration of each unit of the road surface property acquiring device, where
Figure 2B:
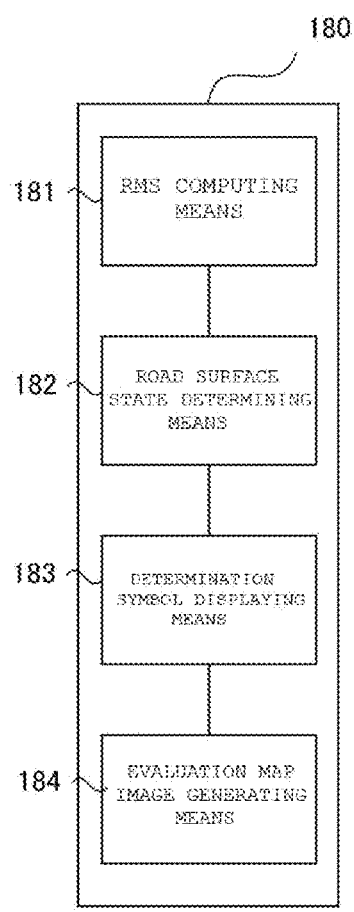
Figure 2C:
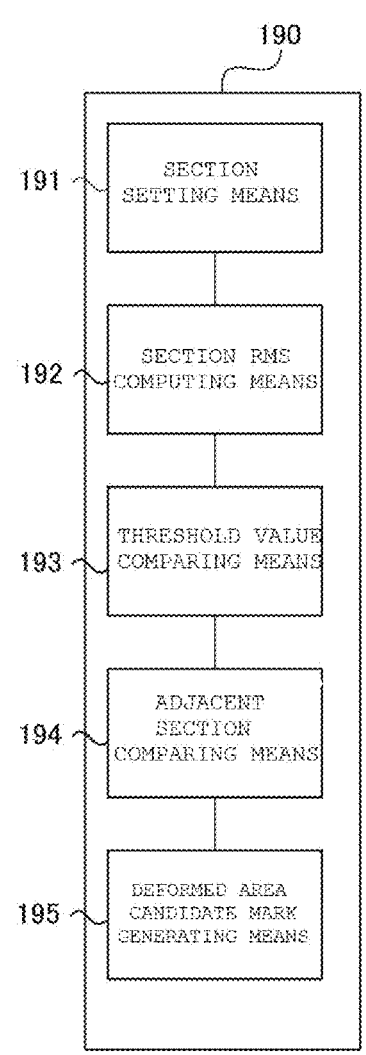

A display device of the road property will be hereinafter described. FIG. 1 is a block diagram showing a configuration of a display device of a road property according to an embodiment of the present invention, and FIGS. 2A-C show a configuration of each unit of the road surface property acquiring device, where FIG. 2A is a block diagram showing a configuration of a point group data generating means, FIG. 2B is a block diagram showing a configuration of a road surface evaluating means, and FIG. 2C is a block diagram showing a configuration of a deformed area detecting means.

A measuring device 100 of a road property (hereinafter simply referred to as "measuring device 100") according to an embodiment of the present invention is connected to a data acquiring device 300. The measuring device 100 acquires measurement data related to a height of a road surface and a road image including the periphery from the data acquiring device 300. An input means 200 including a keyboard, a mouse, a touch panel, and the like, and an image displaying means 210 including a liquid crystal display device are connected to the measuring device 100. An area, a measurement date and time, a display method, and the like of a desired road are input from the input means 200 to the measuring device 100, and various types of images generated by the measuring device 100 are displayed on the image displaying means 210.

As shown in FIG. 1, the measuring device 100 includes a road surface data storage means 110, a map data storage means 120, a warning issuing means 130, a destination setting means 140, a navigation means 150, a present/past data comparing means 160, a spaced amount image generating means 170, a road surface evaluation map generating means 180, and a deformed area candidate mark generating means 190.

The measuring device 100 is configured as a computer equipped with a CPU (Central Processing Unit) for a processing device, a RAM (Random Access Memory) for a main storage device, a ROM (Read Only Memory), an HDD (Hard Disc Drive) for an auxiliary storage device, and the like, and realizes the functions of the road surface data storage means 110, the map data storage means 120, the warning issuing means 130, the destination setting means 140, the navigation means 150, the present/past data comparing means 160, the spaced amount image generating means 170, the road surface evaluation map generating means 180, and the deformed area candidate mark generating means 190 by executing a program with the CPU.

First, the data acquiring device 300 will be described. FIGS. 4A-B are a schematic view showing a measurement state of the road surface by the data acquiring device, where FIG. 4A is a side view and FIG. 4B is a plan view. As shown in FIG. 4A, the data acquiring device 300 is mounted on a vehicle 340 travelling on a road 400. The data acquiring device 300 includes a scanner 310, a whole circumference camera 320, a laser pointer 330, an GNSS device, an orientation detecting device of the data acquiring device 300, an acceleration meter, and the like. The data acquiring device 300 irradiates a scan light La in a spiral form toward a diagonally front side of the vehicle 340 with the scanner 310 while acquiring the position with the GNSS (Global Navigation Satellite System) device, and receives a reflected light Lb from the road 400. The measurement data of the road 400 is acquired based on a time until the reception. Thus, a trajectory T of the scan light La at the road 400 becomes an arcuate shape, as shown in FIG. 4B. At the same time, the data acquiring device 300 acquires an image of a road over the entire circumference with the whole circumference camera 320. The laser pointer 330 scans and irradiates the road surface with a visible laser, and projects and displays a deformed area candidate mark, to be described later, to an area of a deformed area candidate of the road surface.

Figure 5A:
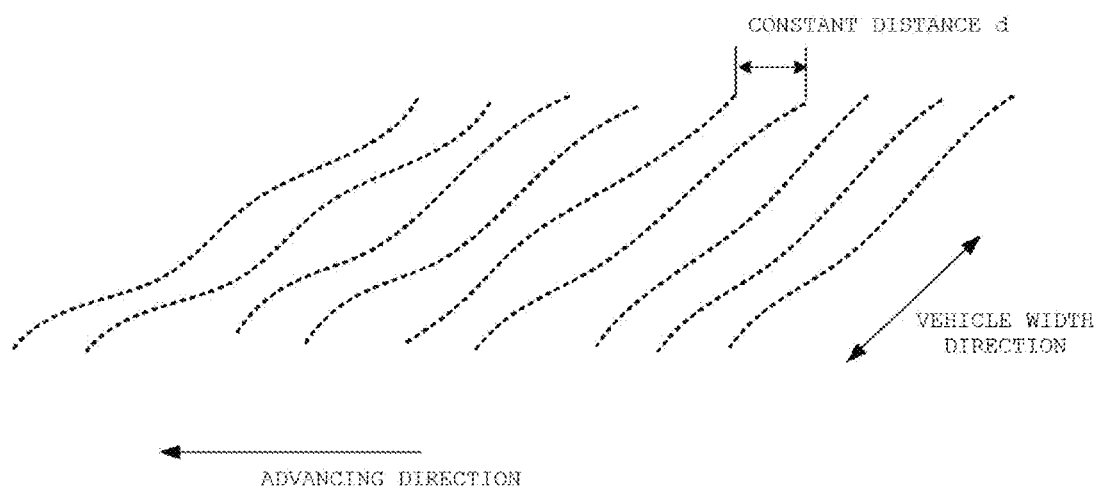
FIGS. 5A and 5B are a schematic view showing an outline of measurement data, where
Figure 5B:
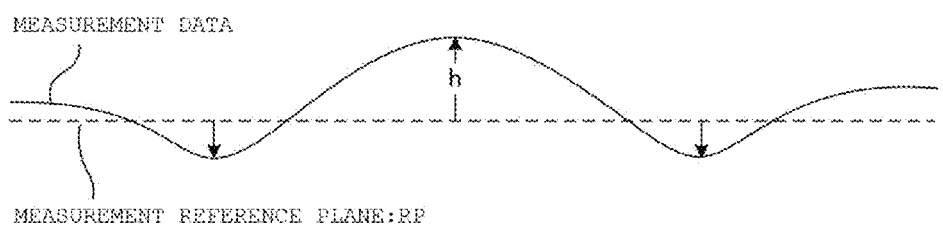

FIGS. 5A-B are a schematic view showing an outline of the measurement data, where FIG. 5A is a perspective view of the measurement data, and FIG. 5B is a schematic view showing the measurement data and a measurement reference plane. As shown in FIG. 5A, the data acquiring device 300 acquires the measurement data of each point on a plurality of trajectories of the scan light La respectively spaced apart by a constant distance "d" in the road 400. As shown in FIG. 5B, the measurement data represents a spaced amount "h" from a measurement reference plane (e.g., geoid plane) RP set by the data acquiring device 300.

The configuration of each unit of the measuring device 100 will now be described. The road surface data storage means 110 stores the road surface data acquired in the past, and the road surface data during the measurement. The road surface data includes the measurement data from the data acquiring device 300, point group data, to be described later, an RMS value of a unit area, a determination result of the road surface, the position of a hole candidate, and the like. The road surface data are saved in the kml (Keyhole Markup Language) format, for example, with the acquired date and time, latitude, and longitude. The road surface data may be saved in other formats.

The map data storage means 120 stores the map data including roads. The map data is used to draw a map in map images 600, 700 shown in FIGS. 9 and 10 in the image displaying means 210.

The warning issuing means 130 issues a warning by characters, and the like on the image displaying means 210 and a warning by audio when the value of the road surface data such as the measurement data, the point group data, and the road surface evaluation exceeds a predefined value, and when a difference value of the past road surface data and the present road surface data computed by the present/past data comparing means 160 exceeds a predefined value.

The destination setting means 140 sets the destination. The destination is specified by various methods such as specification of latitude and longitude from the input means 200, setting by specification on the map of the image displaying means 210, automatic setting of an area having rough road surface and a predetermined area such as a pot hole, and the like from the past road surface data.

The navigation means 150 acquires a path from the present position or the set position to the destination, and displays the same on the image displaying means 210. The displaying of the path is carried out by route display on the map of the image displaying means 210, or by display with directions and distances. The selection of the path of the navigation means 150 is carried out with a known method.

The present/past data comparing means 160 compares the past road surface data stored in the road surface storage means 110 and the present road surface data acquired by the data acquiring device 300, and compares the road surface data acquired at different timing acquired by the road surface data storage means 110 to compute a difference value.

The spaced amount image generating means 170, the road surface evaluation map generating means 180, and the deformed area candidate mark generating means 190 of the measuring device 100 will now be described. FIGS. 2A-C show the configuration of each unit of the road surface property acquiring device, where FIG. 2A is a block diagram showing a configuration of the point group data generating means, FIG. 2B is a block diagram showing a configuration of the road surface evaluating means, and FIG. 2C is a block diagram showing a configuration of the deformed area detecting means; and FIGS. 3A-C show a processing procedure of each unit of the road surface property acquiring device, where FIG. 3A is a flowchart showing a processing procedure of the point group data generating means, FIG. 3B is a flowchart showing a processing procedure of the road surface evaluating means, and FIG. 3C is a flowchart showing a processing procedure of the deformed area detecting means.

As shown in FIG. 2A, the spaced amount image generating means 170 includes a unit area setting means 171, a model plane setting means 172, a point group data calculating means 173, and a color coded image generating means 174. The unit area setting means 171 acquires the measurement data from the data acquiring device 300 (step SA1 of FIG. 3A), and sets a unit area having a preset length dimension along the path in a width of a road along the relevant path.

Figure 6A:
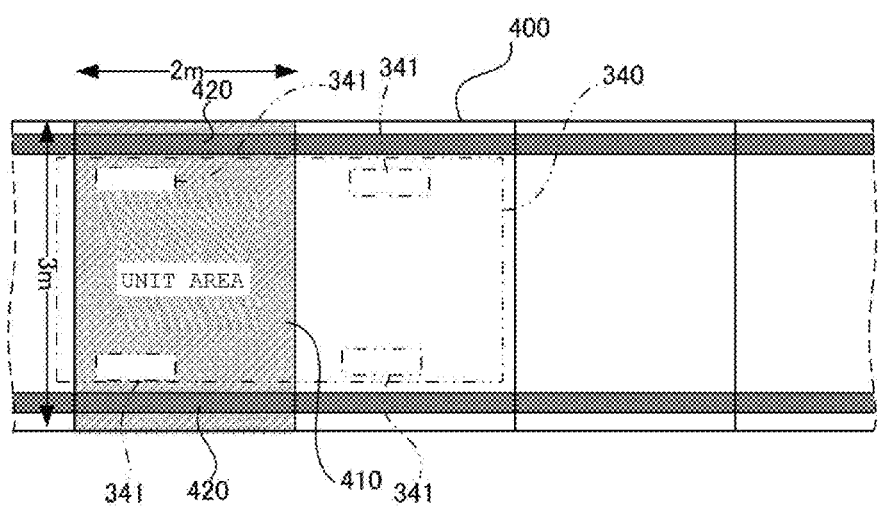
FIGS. 6A and 6B show an acquired state of the point group data in a unit area, where
Figure 6B:
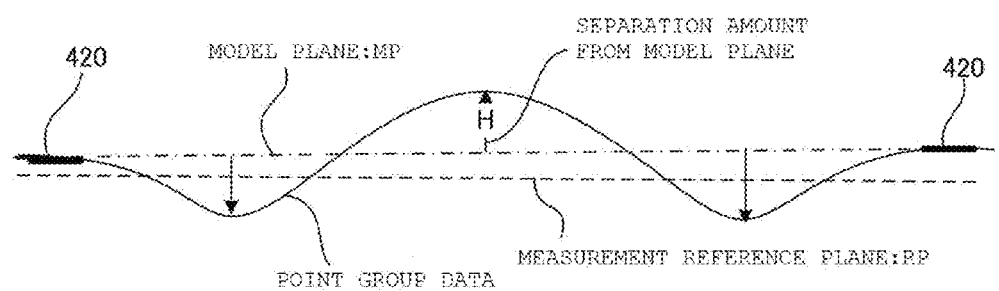

FIGS. 6A-B shows an acquired state of the point group data in the unit area, where FIG. 6A is a schematic view showing the unit area and FIG. 6B is a schematic view showing the point group data and the model plane MP. The unit area setting means 171 divides the road 400 to be measured to, for example, a unit area 410 having a width of 3 m and a length of 2 m (step SA2 of FIG. 3A), as shown in FIG. 6A. A width dimension can be set with the width of one lane of the road, from one road shoulder to another shoulder, the width, and the like of the vehicle used for the measurement, and the like as a reference. The length dimension is not limited to 2 m and can be appropriately set, but the computation of the setting of the model plane MP, and the like become cumbersome, and the gap between the model plane MP and the road surface shape may become large if the length dimension is too long.

Figure 3A:
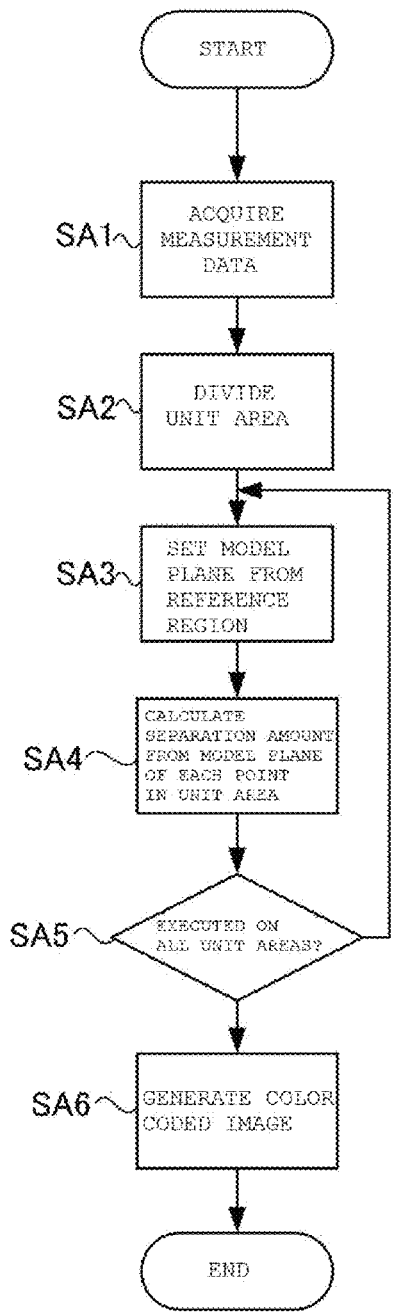
FIGS. 3A, 3B and 3C show a processing procedure of each unit of the road surface property acquiring device, where
Figure 3B:
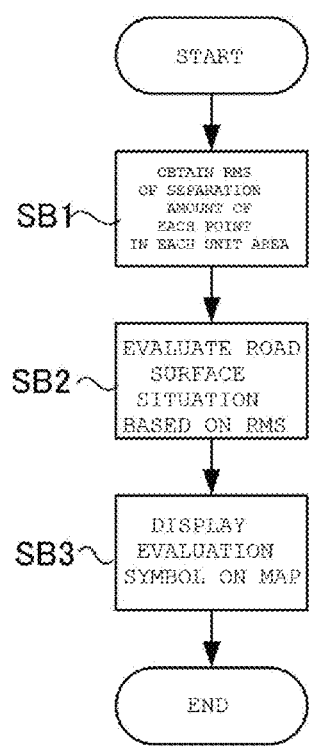
Figure 3C:
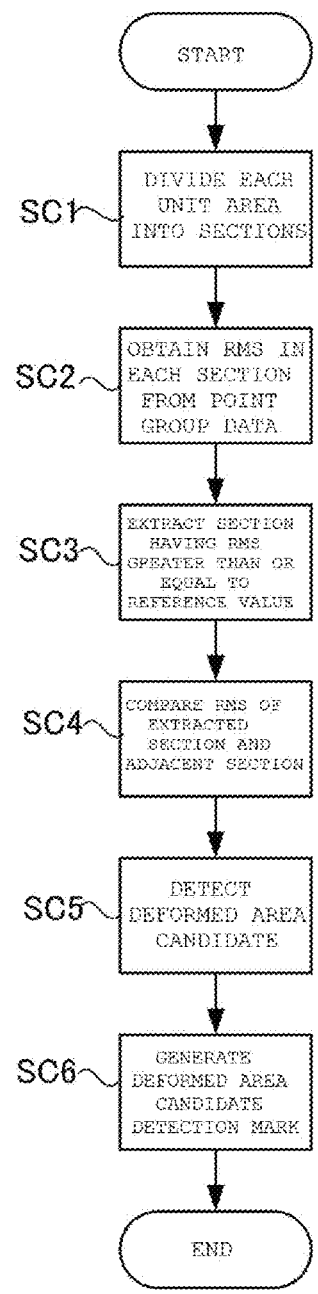

The model plane setting means 172 sets the model plane MP in the unit area 410 based on the measurement data, which is the spaced amount from the measurement reference plane, of each point at the measurement point in the unit area 410 (step SA3 of FIG. 3A). The model plane MP is set based on two regions spaced apart in the road width direction, for example, a reference region 420, which is a region having a width of 20 cm spaced apart by a predetermined distance (e.g., 20 cm) to the outer side from a wheel 341 of the vehicle 340, as shown in FIG. 6A. Specifically, the model plane MP can be obtained through a least square method from a great number of point groups belonging to the reference regions 420, 420.

The reference region is not limited to two, and may be three or more such as three regions of a central region and regions on both end sides. In addition to the example above, the point group in a region having an interval dimension and a width dimension of a certain extent, and where damages and hollowing by the travelling of the vehicle are not anticipated, for example, the line end, the vicinity of the center of the vehicle width, and the paint of the lane mark can be used for the reference region. The lane mark can be acquired by measuring the luminance of the road surface at the time of the measurement of the road image by the data acquiring device 300. The point group data includes a spaced amount "H" from the model plane MP of each point on the unit area 410, as shown in FIG. 6A.

As shown in FIG. 6B, the point group data calculating means 173 calculates the spaced amount "H" between the model plane MP and each point (step SA4 of FIG. 3A). This is executed for all the unit areas (step SA5 of FIG. 3A) to generate the point group data from the spaced amount of each point in the unit area 410.

Figure 7A:
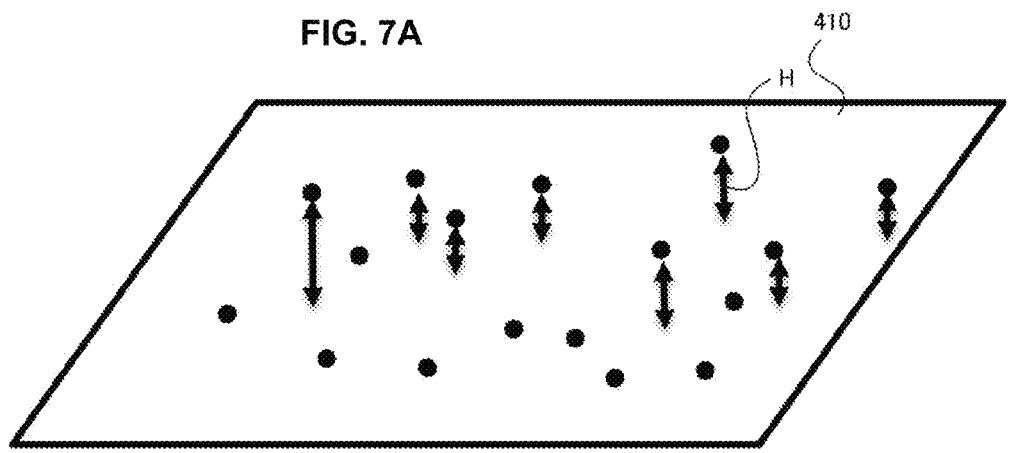
FIGS. 7A, 7B and 7C show a spaced amount from a model plane and a state of display, where
Figure 7B:
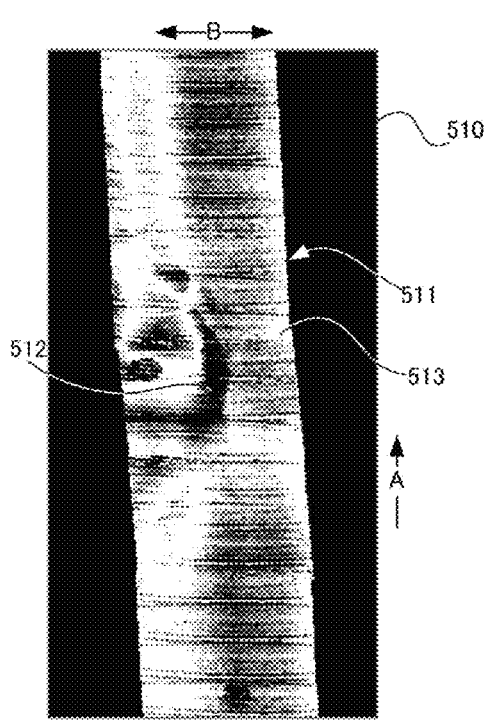
Figure 7C:
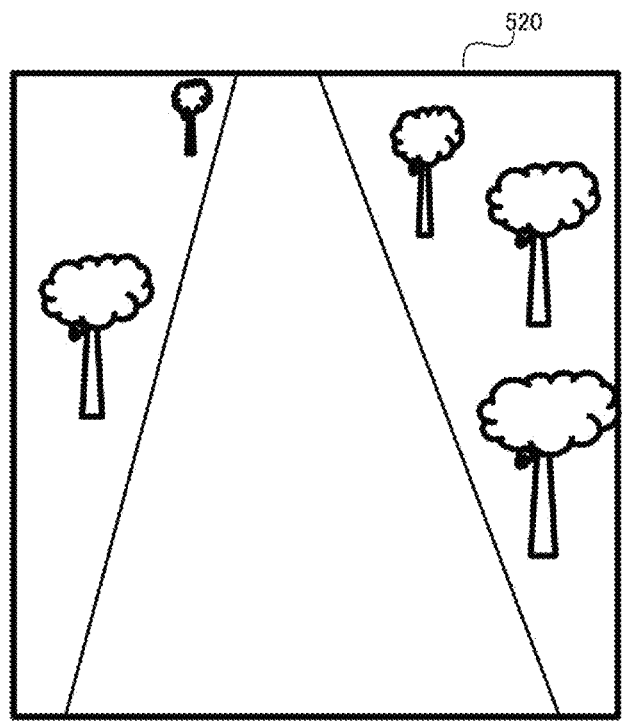

The color coded image generating means 174 generates a color coded spaced amount image based on the spaced amount. FIGS. 7A-C show the spaced amount from the model plane and a state of the display. As shown in FIG. 7B, in the spaced amount image, a region of the road is color coding displayed based on the spaced amount of each point of the road. An arrow A in the figure indicates an advancing direction of a measuring vehicle, and an arrow B indicates a road width direction of the road.

In this case, a spaced amount image 510 shown in FIG. 7B is displayed as a grayscale image, where a highest area 512 than the model plane MP is displayed in white, a lowest area 513 than the model plane MP is displayed in black, and an area in between is displayed in gray shading in the road 511. The spaced amount from the model plane MP in the road thus can be easily recognized. Such image is actually an image in which the high and low state can be more easily recognized as a color gradation image. A road image 520 shown in FIG. 7C corresponding to a display area of the spaced amount image 510 can be displayed with the spaced amount image 510. The road image 520 is acquired with the whole circumference camera 320 of the data acquiring device 300.

Figure 8:
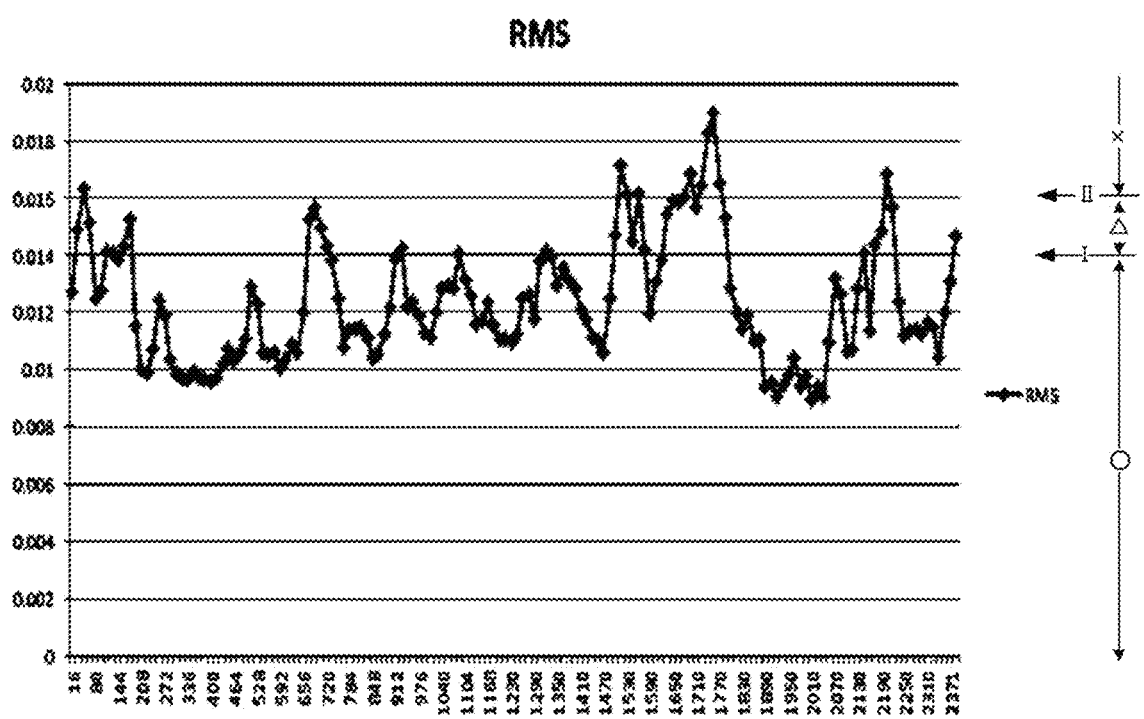
FIG. 8 is a graph showing change in an RMS value in the measurement path.

As shown in FIG. 2B, the road surface evaluation map generating means 180 includes an RMS computing means 181, a road surface property determining means 182, a determination symbol displaying means 183, and an evaluation map image generating means 184. The RMS computing means 181 acquires point group data in each unit area 410, and calculates an RMS (Root Mean Square), which is a statistic in each unit area ((Step SB1) of FIG. 3B). FIG. 8 is a graph showing change in the RMS value in the measurement path. The RMS value of each unit region is shown on a vertical axis, and the distance is shown on a horizontal axis. Other than the RMS, other statistics can be used. Thus, the distribution of the road surface property in the path thus can be known.

The road surface property determining means 182 carries out evaluation of the road surface property for each position of the road based on the RMS value obtained by the RMS computing means 181 ((step SB2) of FIG. 3B). In other words, in order to generate the evaluation result of the road surface property from the RMS value shown in FIG. 6, for example, two values, value I and value II (I<II), are set. Determination is made that the road surface property is satisfactory "○" if smaller than value I, the road surface property is normal "Δ" if greater than or equal to value I and smaller than value II, and the road surface property is poor "x" if greater than or equal to value II. The determination symbol displaying means 183 generates the determination result as an image. Map images 600, 700 in which each determination result image is displayed on a map are displayed in the evaluation map image generating means 184 ((step SB3) of FIG. 3B, FIGS. 9 and 10).

The deformed area candidate mark generating means 190 detects a pot hole (partial hollowing or hole in the road), a recess such as a split, and a projection such as a protrusion between the splits as a defective area of the road surface as the deformed area candidate. The deformed area candidate mark generating means 190 includes a section setting means 191, a section RMS computing means 192, a threshold value comparing means 193, an adjacent section comparing means 194, and a deformed area candidate mark generating means 195.

Figure 11A:
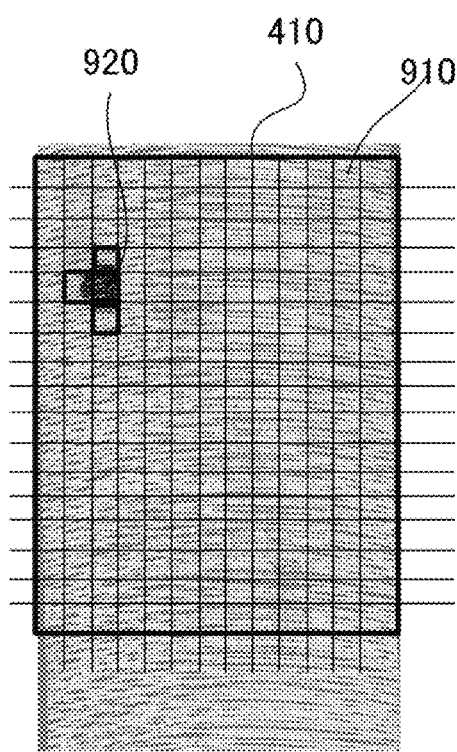
FIGS. 11A and 11B show detection of a deformed area, where
Figure 11B:
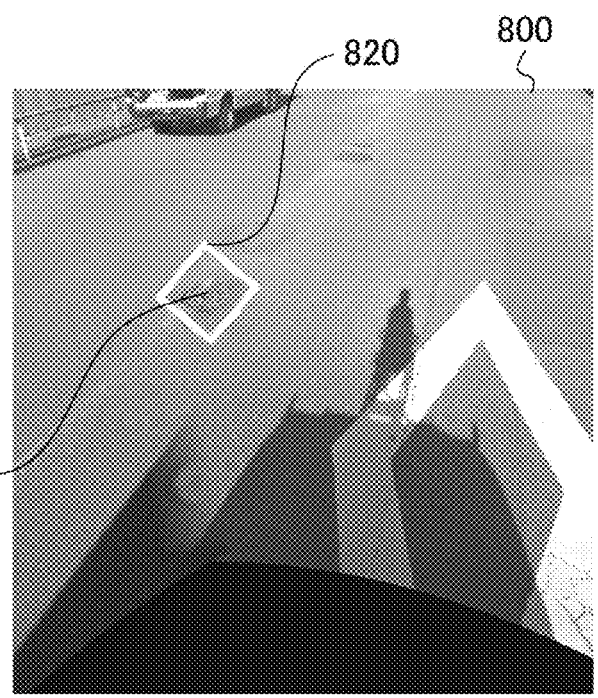

FIGS. 11A-B show detection of a deformed area candidate, where FIG. 11A is a schematic view showing a section in the unit area, and FIG. 11B is a view showing a display state of the deformed area candidate mark on the road surface by the laser pointer.

First, the section setting means 191 divides the unit area into sections (SC1 of FIG. 3C). As shown in FIG. 11A, the unit area 410 is marked to a grid form to be divided into regularly arranged sections 910, 910, . . . .

The section RMS computing means 192 calculates the RMS (Root Mean Square) as the statistic of the point group data belonging to each section as a representative value of each section (step SC2 of FIG. 3C). The threshold value comparing means 193 compares the representative value of each section with a predefined reference value to extract a section satisfying the reference value (step SC3 of FIG. 3C).

Next, the adjacent section comparing means 194 compares the extracted representative value of each section and the representative value of the adjacent section (step SC4 of FIG. 3C), and detects an area where an absolute value of the changing amount, which is the difference of the representative values, is greater than a predefined threshold value as a deformed area candidate (step SC5 of FIG. 3C). The section having a changing amount of greater than or equal to a defined value is thereby recorded as the deformed area candidate. In this case, a recess candidate or a projection candidate is discriminated by the representative value and a sign of the difference of the representative values. Determination is made as a candidate of the recess even if the sections having a changing amount greater than the threshold value are adjacent to each other. The recess candidate includes a pot hole, and the like, and the projection candidate includes a protrusion, and the like formed between the splits.

The deformed area candidate mark generating means 195 generates a deformed area candidate mark displaying an area corresponding to the contour of the section to become the candidate of the deformed area (step SC6 of FIG. 3C). A deformed area candidate mark 820 created at a periphery of the deformed area candidate image 810 of the road image 800 is thereby displayed, as shown in FIG. 11B. Other than a frame indicating the contour of the section, a mark indicating the relevant area of the road surface can be adopted for the deformed area candidate mark. The relevant area of the road surface is thereby pointed out with the laser pointer 330.

The process of the measuring device 100 will be described below. FIGS. 12A-D are a flowchart showing processes of the road surface property acquiring device. Hereinafter, "guiding process of a vehicle based on the road surface data" in the past shown in FIG. 12A, "road surface determination process during travelling" shown in FIG. 12B, "road surface determination process by past data" shown in FIG. 12C, and "road surface determination process by difference" shown in FIG. 12D will be described. Each process is started by specification from the input means 200.

Figure 9:
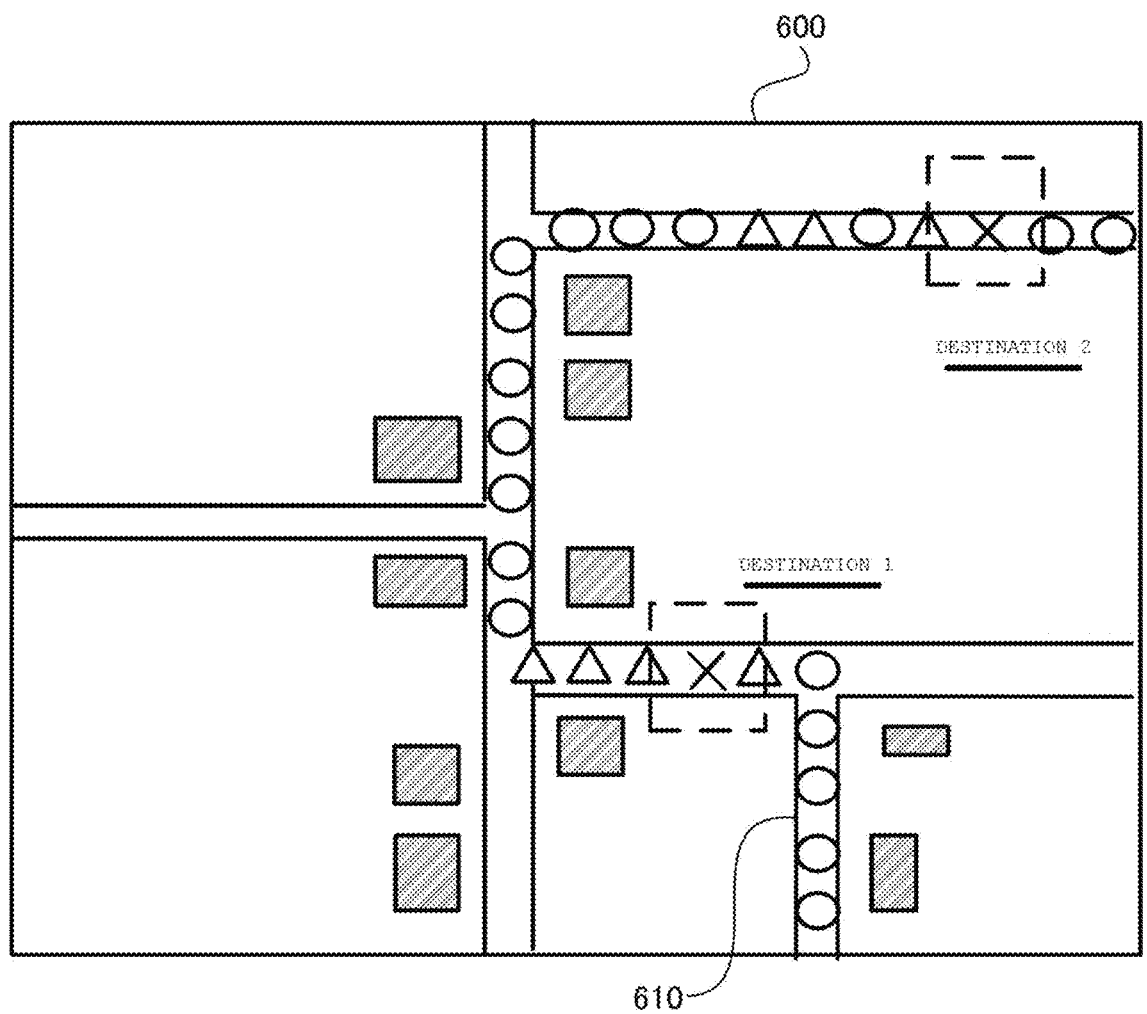
FIG. 9 is a schematic view showing a guiding image displaying a road surface evaluation.

First, the "process of guiding the vehicle based on the past road surface data" will be described based on FIG. 12A. This process is executed by the navigation means 150. First, the navigation means 150 reads out the road surface data from the road surface data storage means 110 (step S11). The spaced amount image generated by the spaced amount image generating means 170 for the past data and the map image from the map data storage means 120 are displayed on the image displaying means 210. An area having a large spaced amount for a feature amount, that is, an area of rough road surface is set as a destination by the destination setting means 140 according to the instruction from the input means 200 (step S12). Such specification can be made, for example, by specifying the road surface evaluation and the deformed area stored in the road surface data storage means 110. As shown in FIG. 9, the area of poor road surface evaluation "x" is selected from the map image 600 displaying the evaluation result of the road surface property in the past. In this example, two areas, destination 1 and destination 2, are selectively specified.

The navigation means 150 then guides the vehicle to a destination specified based on the latitude/longitude information of the specified area (step S13). This guidance can be carried out by route display in the map image 600 or by displaying direction of the destination and the remaining distance. When arriving at the destination or when close to the deformed area, the relevant area of the road surface can be pointed out with the laser pointer 330, as necessary, or the deformed area candidate mark 820 can be displayed on the road image 800, as shown in FIG. 11B.

The "road surface determination process during travelling" will now be described based on FIG. 12B. This process is a process of causing the vehicle to travel on a defined path to acquire the measurement data of the road surface. First, the data acquiring device 300 continues to acquire the position and the orientation of the vehicle 340 (step S21). With the travelling of the vehicle 340, the measurement of the road is carried out by the scanner 310 of the data acquiring device 300 to acquire the measurement data, which is the spaced amount from the measurement reference plane RP (step S22). The spaced amount image generating means 170 sets the model plane MP from the measurement data, and generates the point group data, which is the spaced amount from the model plane MP (step S23), and based thereon, generates the spaced amount display image and displays the image on the image displaying means 210 (step S24). The road surface evaluation map generating means 180 evaluates the road surface situation, and displays the evaluation result of the road surface property in a range including the position of the vehicle on the map displayed on the image displaying means with the present position of the vehicle.

The warning issuing means 130 issues a warning by the display of the image displaying means 210 or by audio when the spaced amount and the evaluation result of the travelling point exceed a predefined value (step S26). The measured road surface data is stored in the road surface data storage means 110. The road surface data can be stored for only a predetermined region including an area where the warning described above is issued. The amount of data to be stored thus can be prevented from becoming too large.

When coming close to the deformed area by the process of the deformed area candidate mark generating means 190, the deformed area is irradiated and pointed out with the laser pointer 330, as necessary.

The "road surface determination process by past data" will now be described based on FIG. 12C. This process is a process of carrying out the measurement of the road surface by travelling on the measurement path while referencing the road surface data measured in the past. First, the data acquiring device 300 continues to acquire the position and the orientation of the vehicle 340 (step S31). With the travelling of the vehicle 340, the measurement of the road is carried out by the scanner 310 of the data acquiring device 300 to acquire the measurement data, which is the spaced amount from the measurement reference plane RP (step S32). The spaced amount image generating means 170 and the road surface evaluation map generating means 180 acquire the past road surface data from the road surface data storage means 110 (step S33), and based thereon, generate the spaced amount display image and display the same on the image displaying means 210 (step S34). The road surface evaluation map generating means 180 then can evaluate the road surface situation (step S35), and display the evaluation result in the map displayed on the image displaying means 210.

The warning issuing means 130 issues a warning by the display of the image displaying means 210 or by audio when the spaced amount and the evaluation result of the currently travelling point exceed a predefined value (step S36). In this case, the road surface data measured by the data acquiring device 300 is stored in the road surface data storage means 110 (step S37). In other words, the road surface data is stored for only a predetermined region including an area where the warning described above is issued. The amount of data to be stored thus can be prevented from becoming too large.

When the deformed area is detected by the process of the deformed area candidate mark generating means 190 from the past road surface data, the deformed area is irradiated and pointed out with the laser pointer 330, as necessary (step S38). Thus, the area where the deformed area existed in the past can be clearly understood, and the present road surface situation can be checked.

The "road surface determination process by difference with past data" will now be described based on FIG. 12D. In this process, the measurement of the road surface is carried out by travelling on the measurement path while referencing the road surface data measured in the past, a difference value of the past and present road surface data is acquired, and the difference value is compared with a predetermined value. First, the data acquiring device 300 continues to acquire the position and the orientation of the vehicle 340 (step S41). With the travelling of the vehicle 340, the measurement of the road is carried out with the scanner 310 of the data acquiring device 300, and the measurement data, which is the spaced amount from the measurement reference plane RP, is acquired (step S42). Furthermore, the past data comparing means 160 acquires the past road surface data from the road surface data storage means 110 (step S43), and computes the difference value of the road surface data.

The spaced amount image generating means 170 and the road surface evaluation map generating means 180 generate the spaced amount display image and display the same on the image displaying means 210 based on the present road data (step S46). The road surface evaluation map generating means 180 can evaluate the road surface situation, and display the evaluation result on the map displayed on the image displaying means 210 (step S47).

The warning issuing means 130 issues a warning by the display of the image displaying means 210 or by audio when the difference value of the past and present road surface data at a travelling point exceeds a predefined value (step S46). In this case, the road surface data measured by the data acquiring device 300 is stored in the road surface data storage means 110. In other words, the road surface data is stored for only a predetermined region including an area where the warning described above is issued (step S48). The amount of data to be stored thus can be prevented from becoming too large.

When the deformed area is detected by the process of the deformed area candidate mark generating means 190 from the past road surface data, the deformed area is irradiated and pointed out with the laser pointer 330, as necessary (step S49). Thus, the area where the difference value with the past road surface data is greater than or equal to a predetermined value can be clearly recognized, and the present road surface situation can be checked.

A display example in the image displaying means 210 by the measuring device 100 will now be described. FIG. 9 is a schematic view showing a map display for setting a destination. When setting the destination, kml data on the previous evaluation result of the road surface property is read. The evaluation results "◯", "x", "Δ" are thereby described in the road 610 of the map image 600. An area with the evaluation result "x", for example, is set as the destination from such display. In this example, two areas, destination 1 and destination 2, are specified. This selection can be carried out by having the operator specify with the input means 200 while visually checking the image displaying means 210, and furthermore, the evaluation value can be specified to set the destination, or that which is greater than or equal to the threshold value can be automatically selected from the RMS value of the spaced amount and specified as the destination.

Figure 10:
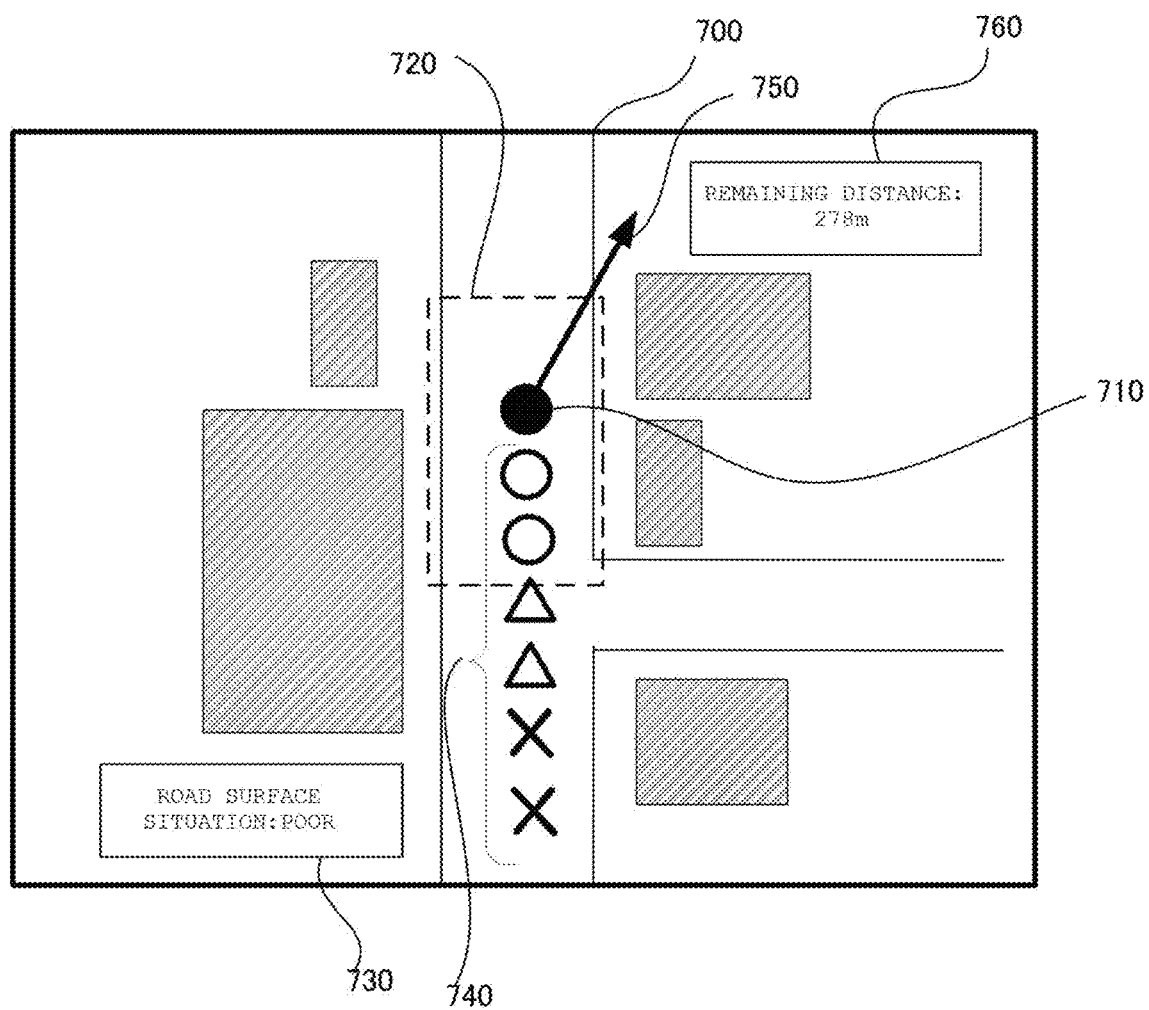
FIG. 10 is a schematic view showing a map display for setting a destination.

FIG. 10 is a schematic view showing a guiding image displaying the road surface evaluation. During the measurement while travelling the vehicle 340, the map image 700 is displayed on the image displaying means 210. The map image 700 is an example of acquiring the spaced amount image and the road surface evaluation from the present measurement data, and guiding the vehicle while displaying the spaced amount image and the road surface evaluation on the map image. In the map image 700, a present vehicle position 710, a spaced amount image 720 in which the spaced amount is color coding displayed, a road surface evaluation result 730 of a present location, an evaluation result 740 of the road surface, a direction 750 of the destination, and a distance 760 to the destination are displayed. In place of the direction of the destination, a route to the destination can also be displayed on the road 610.

Furthermore, in addition to such displays, the RMS value of the spaced amount in the unit area can be displayed. Moreover, a difference value of various types of previous and present measurement data can be displayed, in addition to displaying the previous measurement result in the map image 600. When detecting the RMS value or the difference value greater than the predefined value while displaying such screen, a warning display can be made in the map image 600 or a warning alarm can be issued. In such a case, text can be input from the image displaying means 210 and recorded.

Therefore, according to the display method of the road property and the display device of the road property of the embodiment of the present invention, efficient and effective screen display at the time of road surface property evaluation can be carried out.

The invention claimed is:

1. A road surface property acquiring method of guiding a vehicle mounted with a road surface property acquiring device to a specified point on a road and carrying out measurement; the method comprising the steps of:
    acquiring past road surface data on a past road surface property;
    acquiring a present position of the vehicle;
    setting a model plane based on at least a first reference region and a second reference region that are spaced apart in a road width direction;
    displaying a past road surface property image representing a feature amount of the road surface property in a range including the present position created based on the past road surface data, the past road surface property image comprising a spaced amount image in which measurement data obtained from the past road surface data are shading coded or hue coded in correspondence with a spaced amount of point group data representing a separation amount from the model plane; and
    guiding the vehicle from the present position to a specified area while measuring a state of the road surface with the road surface property acquiring device.

2. The road surface property acquiring method according to claim 1, further comprising a step of displaying a map image displaying the road.

3. The road surface property acquiring method according to claim 1, further comprising the steps of:
    acquiring present measurement data on a property of a road surface on which the vehicle is currently travelling; and displaying a present road surface property image representing a feature amount of the road surface property created based on the present measurement data with the past road surface property image.

4. The road surface property acquiring method according to claim 1, further comprising a step of issuing a warning when the feature amount generated based on the past road surface property image at the present position exceeds a predefined value.

5. The road surface property acquiring method according to claim 1, further comprising a step of saving measurement data in a region including the present position when the feature amount generated based on the past road surface property image at the present position exceeds a predefined value.

6. The road surface property acquiring method according to claim 1, further comprising the steps of generating a difference value of the past road surface data and present measurement data on a property of a road surface on which the vehicle is currently travelling at the present position, and issuing a warning when the difference value exceeds a predefined value.

7. The road surface property acquiring method according to claim 1, further comprising the steps of generating a difference value of the past road surface data and present measurement data at the present position, and saving measurement data in a region including the present position when the difference value exceeds a predefined value.

8. The road surface property acquiring method according to claim 1, further comprising the steps of:
setting a unit area, to become a unit of processing, based on the past road surface data;
dividing the unit area into a plurality of sections and calculating a statistic from the past road surface data in each section;
extracting a section having a statistic satisfying a predefined reference value; and
detecting a deformed area candidate based on a changing amount of the statistic of the extracted section and a statistic of a section adjacent to the extracted section.

9. The road surface property acquiring method according to claim 8, further comprising the steps of:
setting a region of the road exceeding a predefined value or a region of the road assumed as the deformed area candidate as a defective area; and
irradiating and pointing the defective area with a laser pointer when close to the defective area.

10. A road surface property acquiring device of guiding a vehicle mounted with a road surface property acquiring device to a specified point on a road and carrying out measurement; the road surface property acquiring device comprising:
a means for acquiring past road surface data on a past road surface property;
a means for acquiring a present position of the vehicle;
a means for setting a model plane based on at least a first reference region and a second reference region that are spaced apart in a road width direction;
a means for displaying a past road surface property image representing a feature amount of the road surface property in a range including the present position created based on the past road surface data, the past road surface property image comprising a spaced amount image in which measurement data obtained from the past road surface data are shading coded or hue coded in correspondence with a spaced amount of point group data representing a separation amount from the model plane; and
a means for guiding the vehicle from the present position to a specified area while measuring a state of the road surface with the road surface property acquiring device.

11. The road surface property acquiring device according to claim 10, further comprising a means for displaying a map image displaying the road.

12. The road surface property acquiring device according to claim 10, further comprising:
a means for acquiring present measurement data on a property of a road surface on which the vehicle is currently travelling; and
a means for displaying a present road surface property image representing a feature amount of the road surface property created based on the present measurement data with the past road surface property image.

13. The road surface property acquiring device according to claim 10, further comprising a means for issuing a warning when the feature amount generated based on the past road surface property image at the present position exceeds a predefined value.

14. The road surface property acquiring device according to claim 10, further comprising a means for saving measurement data in a region including the present position when the feature amount generated based on the past road surface property image at the present position exceeds a predefined value.

15. The road surface property acquiring device according to claim 10, further comprising a means for generating a difference value of the past road surface data and present measurement data on a property of a road surface on which the vehicle is currently travelling at the present position, and a means for issuing a warning when the difference value exceeds a predefined value.

16. The road surface property acquiring device according to claim 10, further comprising a means for generating a difference value of the past road surface data and present measurement data at the present position, and a means for saving measurement data in a region including the present position when the difference value exceeds a predefined value.

17. The road surface property acquiring device according to claim 10, further comprising:
a means for setting a unit area, to become a unit of processing, based on the past road surface data;
a means for dividing the unit area into a plurality of sections and calculating a statistic from the past road surface data in each section;
a means for extracting a section having a statistic satisfying a predefined reference value; and
a means for detecting a deformed area candidate based on a changing amount of the statistic of the extracted section and a statistic of a section adjacent to the extracted section.

18. The road surface property acquiring device according to claim 17, further comprising a means for setting a region of the road exceeding a predefined value or a region of the road assumed as the deformed area candidate as a defective area, and irradiating and pointing the defective area with a laser pointer when close to the defective area.

* * * * *